United States Patent [19]

Masi et al.

[11] 4,035,362

[45] July 12, 1977

[54] METHODS FOR PREPARING CEPHALOSPORINS

[75] Inventors: Paolo Masi; Maurizio Foglio; Giovanni Franceschi; Antonino Suarato; Gianfranco Cainelli, all of Milan; Federico Arcamone, Nerviano (Milan), all of Italy

[73] Assignee: Societa' Farmaceutici Italia S.p.A., Milan, Italy

[21] Appl. No.: 672,527

[22] Filed: Mar. 31, 1976

[30] Foreign Application Priority Data

Apr. 5, 1975  United Kingdom ............ 14241/75

[51] Int. Cl.² .................................... C07D 501/20
[52] U.S. Cl. .......................... 260/243 C; 424/246
[58] Field of Search .............................. 260/243 C

[56] References Cited

U.S. PATENT DOCUMENTS 3,962,277  6/1976  Verweij et al. ................ 260/243 C
3,966,738  6/1976  Verweij et al. ................ 260/243 C Primary Examiner—Nicholas S. Rizzo
Attorney, Agent, or Firm—Stevens, Davis, Miller & Mosher

[57] ABSTRACT

A process for preparing cephalosporins of the structure:

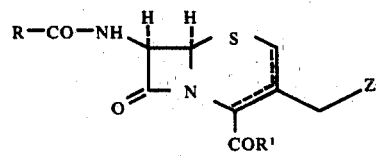

where R is any of hydrogen, $C_1$ to $C_4$ alkyl, t-butoxy, benzyloxy, cyano-methyl, thienyl-methyl, furyl-methyl, naphthyl-methyl, phenyl-methyl, phenoxy-methyl, phenoxy-isopropyl, pyridyl-4-thiomethyl and tetrazolyl-1-methyl;

$R_1$ is any of hydroxyl, $C_1$ to $C_4$ alkoxy, benzyloxy, p-methoxy- (or nitro-) benzyloxy, benzhydryloxy, triphenylmethoxy, phenacyloxy, p-halophenacyloxy and trichloroethoxy;

Z is any of hydrogen, hydroxyl, $-O-CO-C_1-C_4$ alkyl, $-O-C_1-C_4$ alkyl, $-Br$, $-I$, $-Cl$, $-N_3$, $-NH_2$, $-O-CO-CH_3$, $-O-CO-NH_2$ and an -S-mononuclear nitrogen heterocyclic ring, by reacting compounds of the structure:

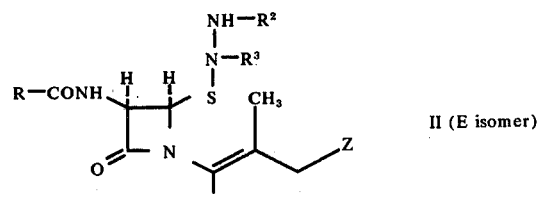

II (E isomer)

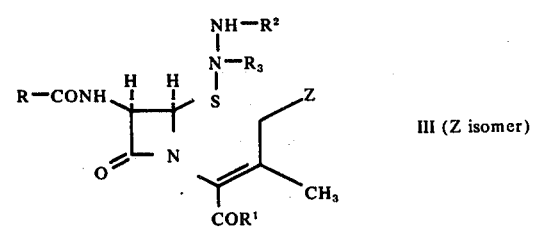

III (Z isomer)

in which R, $R_1$, and Z are as above defined;

$R_2$ and $R_3$ are the same or different and represent a $C_1$ to $C_4$ alkyl, a mononuclear aryl ring, $-CN$, a mononuclear heterocyclic ring or the radicals $-COR_4$, $COOR_4$, $-PO(OR_4)_2$, $-CO-NHR_4$ or $R_2$ and $R_3$ together may represent:

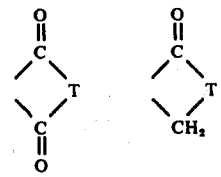

where T represents $>CH_2$, $-N-R_4$;
and $R_4$ is lower alkyl, a mononuclear aryl ring or a mononuclear heterocyclic ring,
alone or as mixtures with each other in a suitable solvent at a temperature between $-100$ and $+120°$ C with a strong base to give compounds of formula I that are a mixture of $\Delta_2$ and $\Delta_3$ cephem-derivatives from which the $\Delta_3$ cephem derivatives can be obtained.

1 Claim, No Drawings

METHODS FOR PREPARING CEPHALOSPORINS

Cephalosporins are a class of antibiotics which are clinically very useful.

This invention relates to cephalosporin compounds and to a novel process for their manufacture.

The cephalosporin compounds involved in this invention fall within the general formula I:

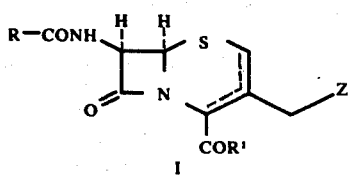

in which R is selected from the class consisting of hydrogen, alkyl having from 1 to 4 carbon atoms, t-butoxy, benzyloxy, cyano-methyl, thienyl-methyl, furyl-methyl, naphthyl-methyl, phenyl-methyl, phenoxy-methyl, phenoxy-isopropyl, pyridyl-4-thiomethyl and tetrazolyl-1-methyl;

$R_1$ is selected from the class consisting of hydroxyl, alkoxy with 1 to 4 carbon atoms, benzyloxy, p-methoxybenzyloxy, p-nitrobenzyloxy, benzhydryloxy, triphenylmethoxy, phenacyloxy, p-halophenzcyloxy, trichloroethoxy;

Z is selected from the class consisting of hydrogen, hydroxyl, —O—alkyl, —O—CO—alkyl, —Br, —I, —Cl, —$N_3$, —$NH_2$, —O—CO—$CH_3$, —O—$CONH_2$ and an —S—mononuclear nitrogen heterocyclic ring, the alkyls having from 1 to 4 carbon atoms.

The above compounds of general formula I can be prepared according to this invention by effecting ring closure of an appropriate intermediate compound of the general formula II or III:

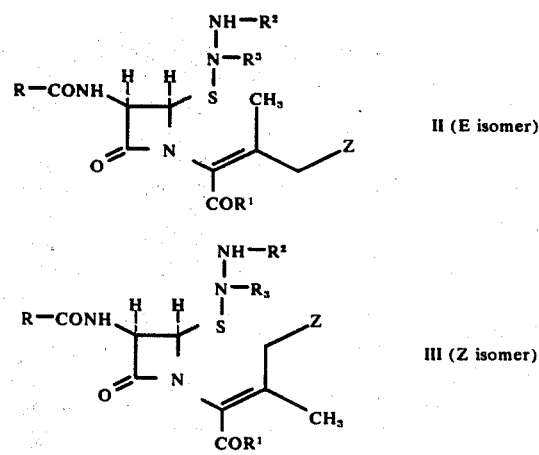

in which R, $R^1$ and Z are as above defined;

$R^2$ and $R^3$ are equal or different and represent a lower alkyl group having from 1 to 4 carbon atoms, a mononuclear aryl ring, —CN—, a mononuclear heterocyclic ring, the radicals —$COR^4$, —$COOR^4$, —$PO(OR^4)_2$, —$CONHR^4$, or $R^2$ and $R^3$ together may represent the residues:

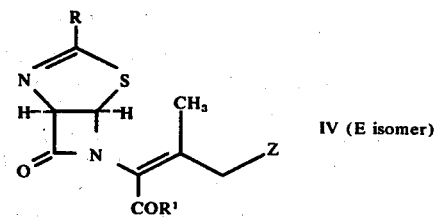

where T represents >$CH_2$, >N-$R_4$;

and $R_4$ is a lower alkyl, a mononuclear aryl ring or a mononuclear heterocyclic ring.

The intermediates II and III may be prepared from thiazoline-azetidinones of the general formulae IV or V:

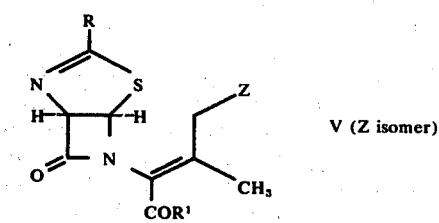

in which R, $R^1$ and Z are as above defined, by reacting the appropriate compound IV or V in an organic solvent at a temperature between −20° C and +80° C, in the presence of an aqueous organic or inorganic acid, with an azoderivative of the general formula VI:

in which $R^2$ and $R^3$ are as above defined.

Many of these intermediates, and their preparation, are described and claimed in our copending British Patent Application No. 21419/75 and U.S. application Ser. No. 578,875.

The ring closure to form the cephalosporins of general formula I is effected according to this invention by treating the intermediate II or III in an anhydrous organic solvent such as tetrahydrofurane, diethyl ether, dimethylformamide, dimethylsulphoxide, diglyme or hexamethylphosphorustriamide, at a temperature between −100° C and +120° C with a strong base. The strong base may be an alkali metal alcoholate or thioalcoholate, an alkali metal phenate or thiophenate having one or more substituents in the aromatic ring, an alkali metal amide, lithium hexamethyldisilazane, an organometallic compound, an alkali metal hydride or a conjugate base of a dialkyl sulphoxide formed for example by reaction of an alkali metal hydride with dimethyl or diethyl sulphoxide. Where reference is made herein to alkali metal, one such as sodium, potassium or lithium is to be understood. Examples of suitable metal amides are the diisopropylamides, dicyclohexylamides and isopropyl-cyclohexyl-amides of lithium, sodium and potassium. Examples of suitable organometallic compounds are phenyl-lithium, a $C_{1-4}$ alkyl-lithium and lithium-, sodium-, and potassium-triphenylmethane.

The subsequent treatment of the resulting mixture of $\Delta_2$ and $\Delta_3$ cephalosporins, following the procedure of Kaiser et al, *J. Org. Chem.* 35, 2430 (1970), affords fairly good yields of the $\Delta_3$ cephem-derivatives.

The following examples still further illustrate this invention.

EXAMPLE 1

Methyl-2β-thiohydrazodicarboxyethyl-α-acetoxyisopropyliden-4-oxo-3β-phenoxyacetamido-1-azetidine acetate, Z isomer.

(Compound III, R = phenoxymethyl; $R^1$ = methoxy; $R^2 = R^3$ = carboethoxy; Z = acetoxy).

To a solution of methyl-α-acetoxyisopropylidene-3-phenoxymethyl-1α-5α-4-thia-2,6-diaza-[3,2,0]-2-heptene-6-acetate-7-one (Compound V, R = phenoxymethyl; $R_1$ = methoxy; Z - acetoxy) (Z isomer), (2.0 g) in acetone (40 ml) containing water (1 ml), ethyl azodicarboxylate (2 ml), and p-toluene-sulphonic acid monohydrate (0.9 g) were added in that order.

After standing for 2 hours at room temperature, the solution was neutralized with $NaHCO_3$, the solvent removed in vacuo and the residue taken up in ethyl acetate and water. The organic layer was washed with water, dried over $Na_2SO_4$ and evaporated in vacuo. The residue was purified by column chromatography (silica gel eluted with benzene/ethyl acetate 8/2, v/v) to give 2.2 g of the desired product.

NMR ($CDCl_3$): 1.23 δ (t, 2 $CH_3$—$C(H_2)$), 2.09 δ (s, $CH_3$—CO), 2.23 δ (s, $CH_3$—C=), 3.82 δ (s, $CH_3$—O), 4.17 δ (q, 2 $CH_2$—$C(H_3)$), 4.57 δ (s, $C_6H_5$—O—$CH_2$), 5.02 δ (s, =C—$CH_2$), 5.25 δ (dd, J' 5.5 Hz, J'' 7.5 Hz, N(H)—CH), 5.93 δ (d, J' 5.5 Hz, C(H)—CH—S), 6.80–7.75 δ (m, 2NH and —$C_6H_5$).

EXAMPLE 2

Methyl-2β-thiohydrazodicarboxyethyl-α-acetoxyisopropyliden-4-oxo-3β-phenoxyacetamido-1-azetidine acetate, E isomer.

(Compound II, R = phenoxymethyl; $R^1$ = methoxy; $R^2 = R^3$ = carbethoxy; Z = acetoxy).

Example 1 was repeated using the same amound to methyl-α-acetoxyisopropylidene-3-phenoxymethyl-1α,5α-4-thia-2,6-diaza-[3,2,0]-2-heptene-6-acetate-7-one (Compound IV, R = phenoxymethyl; $R_1$ = methoxy, Z = acetoxy) (E isomer). 2.1 g of the product was obtained.

NMR ($CDCl_3$): 1.24 δ (t, 2 $CH_3$—$C(H_2)$), 2.10 δ (s, $CH_3$—CO), 2.15 δ (s, $CH_3$—C=), 3.82 δ (s, $CH_3O$), 4.18 δ (s, 2 $CH_3$—$C(H_3)$), 4.59 δ (s, $C_6H_5$—O—$CH_2$), 5.17 δ (dd, J' 5.5 Hz, J'' 7 Hz, N(H)—CH), 5.24 δ (s, =C—$CH_2$), 5.95 δ (d, J' 5.5 Hz, C(H)—CH—S), 6.80–7.65 δ (m, 2 NH and —$C_6H_5$).

EXAMPLE 3

Methyl-7-phenoxyacetamido-3-methyl-($\Delta^2$ and $\Delta^3$)-cephem-4-carboxylates (Mixture of compounds I; R=phenoxymethyl; $R^1$= methoxy; Z = hydrogen).

A solution of lithium di-isopropylamide prepared from di-isopropylamine (1.010 g; 10 mmoles) in anhydrous tetrahydrofurane (15 ml) and n-butyl lithium (4.57 ml of a 20% solution in hexane) was added dropwise to a stirred solution of methyl-2β-thiohydrazodicarboxyethyl-α-isopropylidene-4-oxo-3β-phenoxyacetamido-1-azetidine acetate (1.076 g; 2 mmoles) in anhydrous tetrahydrofurane (5 ml) at −78° C. After 30 minutes at −78° C, the reaction mixture was quenched with acetic acid (7 ml) in tetrahydrofurane (7 ml) and the temperature was raised to from 10° C to 20° C. Ethyl acetate was then added and the solution was washed with water and dried over $Na_2SO_4$. The solvent was removed in vacuo and the residue chromatographed to give the desired product mixture.

EXAMPLE 4

Methyl-7-phenoxyacetamido-3-acetoxymethyl-($\Delta^2$ and $\Delta^3$)-cephem-4-carboxylates (Mixture of compounds I; R= phenoxymethyl; $R^1$ = methoxy; Z = acetoxy).

A solution of lithium diisopropylamide prepared from diisopropylamine (2.5 g, 50 mmoles) in anhydrous tetrahydrofurane (50 ml) and n-butyl lithium (11.4 ml of a 20% solution in hexane) was added dropwise to a stirred solution of the E isomer (Example 2) of methyl-2β-thiohydrazodicarboxyethyl-α-acetoxyisopropylidene-4-oxo-3β-phenoxyacetamido-1-azetidine acetate, (2.5 g, 4.17 mmoles) in anhydrous tetrahydrofurane (50 ml) at −78° C. After 30 minutes at −78° C, the reaction mixture was quenched with acetic acid (20 ml) in anhydrous tetrahydrofurane (20 ml) and the temperature was raised to from 10° C to 20° C. Ethyl acetate was then added and the resulting solution was washed with water and dried over $Na_2SO_4$. The solvent was removed in vacuo and the residue chromatographed to give the desired product mixture.

The same results were obtained starting from the Z isomer of Example 1.

EXAMPLE 5

Methyl-2β-thiohydrazodicarboxyethyl-α-methoxyisopropylidene-4-oxo-3β-phenoxyacetamido-1-azetidine acetate.

(Compound II, R = phenoxymethyl; $R_1$ = methoxy; $R_2 = R_3$ = carboethoxy; Z = methoxy).

To a solution of methyl-α-methoxyisopropylidene-3-phenoxymethyl-1α,5α-4-this-2,6-diaza-[3,2,0]-2-heptene-6-acetate-7-one (Compound IV, R = phenoxymethyl; $R_1$ =methoxy; Z = methoxy) (550 mg) in acetone (10 ml) containing two drops of water, ethyl azodicarboxylate (0.5 ml) and p-toluensulphonic acid monohydrate (285 mg) are added in that order. After standing 7 hours at room temperature, the solution is neutralized with $NaHCO_3$, the solvent removed in vacuo and the residue taken up in ethyl acetate and water. The organic layer is washed with water, dried over $Na_2SO_4$ and evaporated in vacuo. The residue is purified by column chromatography (silica gel eluted with $C_6H_6$/AcOEt 8/2, v/v) to give 400 mg of methyl-2β-thiohydrazodicarboxyethyl-α-methoxyisopropylidene-4-oxo-3β-phenoxyacetamido-1-azetidine acetate.

NMR ($CDCl_3$): 1.21 δ (t, 2 $CH_3$—$C(H_2)$), 2.15 δ (s, $CH_3$—C=), 3.35 δ (s, $CH_3O$), 3.78 δ (s, $CH_3OCO$), 4.14 δ (q, 2 $C(H_3)$— $CH_2$—O—CO), 4.55 δ (middle of two strongly assymmetric doublets, CO—$CH_2O$), 5.19 δ (dd, CH—N(H)), 5.90 δ (d, CH—C(H)), and 6.8–7.8 δ (m, 2 NH and 5 aromatic protons).

EXAMPLE 6

Methyl-7-phenoxyacetamido-3-methoxymethyl-($\Delta_2$ and $\Delta_3$)-cephem-4-carboxylate.

(Mixture of compound I; R = phenoxymethyl $R_1$ = methoxy; Z = methoxy).

A solution of methyl-2$\beta$-thiohydrazodicarboxyethyl-$\alpha$-methoxyisopropylidene-4-oxo-3$\beta$-phenoxyacetamido-1-azetidine acetate (Example 5) (200 mg) in 10 ml of anhydrous tetrahydrofurane is cooled at −78° C and treated with 400 mg of potassium tert-butoxide. After stirring ½ hours, the reaction mixture is quenched with acetic acid (0.5 ml) and the temperature is raised up to 10°-20° C. Ethyl acetate is next added and the resulting solution washed with water and dried over $Na_2SO_4$; the solvent is removed in vacuo and the residue chromatographed to give the desired products-mixture.

EXAMPLE 7

Methyl-2$\beta$-thiohydrazodicarboxyethyl-$\alpha$-tert-butoxyisopropylidene-4-oxo-3$\beta$-phenoxyacetamido-1-azetidine acetate.

(Compound II, R = phenoxymethyl; $R_1$ = methoxy; $R_2 = R_3$ = carboethoxy; Z = tert-butoxy).

To a solution of methyl-$\alpha$-tert-butoxyisopropylidene-3-phenoxymethyl-1$\alpha$, 5$\alpha$-4-thia-2,6-diaza-[3.2.0]-2-heptene-6-acetate-7-one (Compound IV; R = phenoxymethyl; $R_1$ = methoxy; Z = tert-butoxy) (26 g) in tetrahydrofurane (160 ml) ethyl azodicarboxylate (26 ml) and p-toluensulfonic acid monohydrate (13 g) are added in this order. After standing 1 hour at room temperature, The reaction mixture is neutralized with solid $NaHCO_3$, filtered and the solvent is evaporated in vacuo. The residue is taken up in ethyl acetate, washed with water and purified by column chromatography to give 22 g of methyl-2$\beta$-thiohydrazodicarboxyethyl-$\alpha$-tert-butoxyisopropylidene-4-oxo-3$\beta$-phenoxyacetamido-1-azetidine acetate.

NMR ($CDCl_3$): 1.21 and 1.25 $\delta$ (2 t, 2 $CH_3$—$C(H_2)$), 1.22 $\delta$ (s, $CH_3$)—C), 21.5 $\delta$ (s, $CH_3$—C=), 3.80 $\delta$ (s, $CH_3OCO$), 3.96–4.41 (m, 2 $C(H_3)$—$CH_2$—O—CO), 4.56 $\delta$ (middle of two strongly asymmetric doublets, CO—$CH_2$—O), 5.26 $\delta$ (dd, CH—N(H)), 5.88 $\delta$ (d, CH—C(H)), and 6.8–7.9 $\delta$ (m, 2 NH and 5 aromatic protons).

IR ($CHCl_3$): 1770 $cm^{-1}$ ($\beta$-lactam C=O) 1725 $cm^{-1}$ (C=O of groups N—COO and of unsaturated ester) 1690 $cm^{-1}$ (amide C=O)

EXAMPLE 8

Methyl-7-phenoxyacetamido-3-tert-butoxymethyl-($\Delta_2$ and $\Delta_3$)-cephem-4-carboxylate.

(Mixture of compound I; R = phenoxymethyl; $R_1$ = methoxy; Z = tert-butoxy).

A solution of methyl-2$\beta$-thiohydrazodicarboxyethyl-$\alpha$-tert-butoxyisopropylidene-4-oxo-3$\beta$-phenoxyacetamido-1-azetidine acetate (Example 7) (1.8 g) in a mixture of dimethylformamide (15 ml) and tetrahydrofurane (5 ml) is cooled at −78° C and treated with 3.35 g of potassium tert-butoxide. After stirring ½ hour, the reaction mixture is quenced with acetic acid (2.5 ml) and the temperature is raised up to 20° C. The solvent is evaporated in vacuo and the residue is taken up in ethyl acetate, washed with water and carefully chromatographed to give a mixture of methyl-7-phenoxyacetamido-3-tert-butoxymethyl-2-cephem-4-carboxylate and methyl-7-phenoxyacetamido-3-tert-butoxymethyl-3-cephem-4-carboxylate.

$\Delta_2$ isomer

NMR ($CDCl_3$): 1.20 $\delta$ (s, $(CH_3)_3$—C), 3.80 $\delta$ (s, $CH_3O$), 3.98 $\delta$ (broad s, C=C—$CH_2O$), 4.58 $\delta$ (s, CO—$CH_2$—O), 5.10 $\delta$ (broad s, C(4)H), 5.33 $\delta$ (d, C(6)H), 5.75 $\delta$ (dd, C(7)H—), 6.33 $\delta$ (broad s, =C(2)H), 6.8–7.6 $\delta$ (m, NH and 5 aromatic protons)

IR ($CHCL_3$): 1780 $cm^{-1}$ ($\beta$-lactam C=O) 1740 $cm^{-1}$ (saturated ester C=O) 1690 $cm^{-1}$ (amide C=O)

$\Delta_3$-isomer

NMR($CDCl_3$): 1.21 $\delta$ (s, $(CH_3)_3C$), 3.56 $\delta$ (broad s, $C(2)H_2$), 3.86 $\delta$ (s, $CH_3O$), 4.36 $\delta$ (broad s, C=C—$CH_2$—O), 4.58 $\delta$ (s, $CH_2O$), 5.15 $\delta$ (d, C(6)H), 5.90 $\delta$ (dd, C(7)H), 6.8–7.6 $\delta$ (m, NH and 5 aromatic protons).

IR($CHCl_3$): 1785 $cm^{-1}$ ($\beta$-lactam C=O) 1725 $cm^{-1}$ (unsaturated ester C=O) 1690 $cm^{-1}$ (amide C=0)

EXAMPLE 9

Methyl-2$\beta$-thiohydrazodicarboxyethyl-$\alpha$-pivaloyloxyisopropylidene-4-oxo-3$\beta$-phenoxyacetamido-1-azetidine acetate (E + Z isomers). (Mixture of compounds II and III; R = phenoxymethyl; $R_1$ = methoxy; $R_2 = R_3$ = carboethoxy; Z = pivaloyloxy). To a solution of methyl-$\alpha$-pivaloyloxyisopropylidene-3-phenoxymethyl-1$\alpha$,5$\alpha$-4-thia-2,6-diaza-[3.2.0]-2-heptene-6-acetate-7-one (Mixture of compounds IV and V; R = phenoxymethyl; $R_1$ = methoxy; Z = pivaloyloxy) (3g) in acetone (15 ml) containing a few drops of water, ethyl azodicarboxylate (3 ml) and p-toluensulfonic acid monohydrate (1.5 g) are added in this order. After standing 5 hours at room temperature the solution is neutralized with $NaHCO_3$, the solvent removed in vacuo and the residue taken up in ethyl acetate and water. The organic layer is washed with water, evaporated to dryness and the residue chromatographed to give methyl-2$\beta$-thiohydrazodicarboxyethyl-$\alpha$-pivaloyloxyisopropylidene-4-oxo-3$\beta$-phenoxyacetamido-1-azetidine acetate (3.2 g), as a mixture of E + Z isomers.

NMR ($CDCl_3$): 1.23 $\delta$ (s, $C(CH_3)_3$ and 2t, 2 $CH_3$—$C(H_2)$), 2.14 $\delta$ (s, $CH_3$—C=), 3.83 $\delta$ (s, $CH_3OCO$), 4.62 $\delta$ (middle of two strongly asymmetric doublets; CO—$CH_2$—O), 5.37 $\delta$ and 5.95 $\delta$ (broad signals, $\beta$-lactam protons), 6.9–7.7 $\delta$ (m, 2 NH and 5 aromatic protons).

EXAMPLE 10

Methyl-7-phenoxyacetamdio-3-pivaloyloxymethyl-($\Delta_2$ and $\Delta_3$)-cephem-4-carboxylate.

(Mixture of compound I; R = phenoxymethyl; $R_1$ = methoxy; Z = pivaloyloxy).

A solution of methyl-2$\beta$-thiohydrazodicarboxyethyl-$\alpha$-pivaloyloxyisopropylidene-4-oxo-3$\beta$-phenoxyacetamido-1-azetidine acetate (mixture of E + Z isomers; Example 9) (700 mg) in a mixture of dimethylformamide (15 ml) and tetrahydrofurane (5 ml) is cooled at −78° C and treated with 1.12 g of potassium tert-butoxide. After stirring ½ hour, the reaction mixture is quenched with acetic acid (1.5 ml) and the temperature is raised up to 20° C. The solvent is evaporated in vacuo and the residue is taken up in ethyl acetate, washed with water and chromatographed to give the desired compounds mixture.

Mixture of $\Delta_2$- and $\Delta_3$- isomers

NMR($CDCl_3$): 1.22 and 1.27 $\delta$ (two s, $(CH_3)_3C$), 3.39 $\delta$ (middle of two strongly asymmetric doublets, C(2)H₂ of Δ₃ isomer), 3.85 δ (s, CH₃O), 4.61 δ (s, CO—CH₂—O0, 5.3–5.9 δ (m, β-lactam protons of Δ₂ and Δ₃ isomer), 6.48 δ (broad s, =C(2)H of Δ₂ isomer), 6.85–7.66 δ (m NH and 5 aromatic protons).

What is claimed is:

1. A process for preparing cephalosporins of the structure:

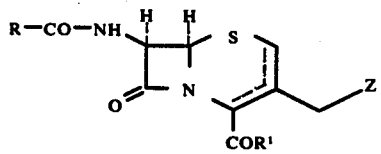

I where R is selected from the class consisting of hydrogen, alkyl having from 1 to 4 carbon atoms, cyanomethyl, thienyl-methyl, naphthyl-methyl, phenylmethyl, phenoxy-methyl, phenoxy-isopropyl, pyridyl-4-thiomethyl and tetrazolyl-1-methyl;

$R_1$ is selected from the class consisting of hydroxyl, alkoxy having from 1 to 4 carbon atoms, benzyloxy, p-methoxybenzyloxy, p-nitro-benzyloxy, benzhydryloxy, triphenylmethoxy, phenacyloxy, p-halo-phenacyloxy and trichloroethoxy;

Z is selected from the class consisting of hydrogen, hydroxyl, O—alkyl, O—CO alkyl, the alkyls having from 1 to 4 carbon atoms, and 2-mercapto-5-methyl-1,3,4-thiadiazole, wherein compounds of structure:

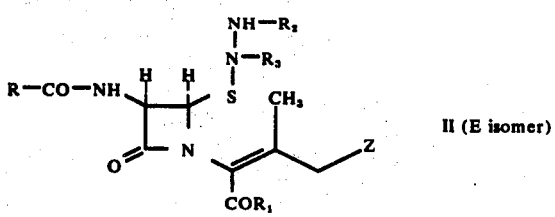

II (E isomer)

or

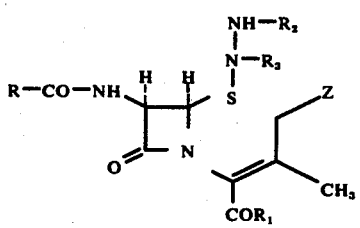

III (Z isomer)

in which R, $R_1$ and Z are as above defined;

$R_2$ and $R_3$ are the same or different and represent the radicals —COOR₄ where $R_4$ is a lower alkyl having from 1 to 4 carbon atoms, are dissolved in anhydrous tetrahydrofuran or anhydrous dimethylformamide and reacted at a temperature between −100° C and +120° C with n-butyl lithium, lithium, sodium or potassium triphenyl methane, lithium diisopropylamide or potassium tert-butoxide to finally give a compound of formula I that is a mixture of Δ² and Δ³ cephem derivatives from which the Δ³ cepham derivatives can be obtained.

* * * * *